US 6,541,273 B1

(12) United States Patent
Plaisance

(10) Patent No.: US 6,541,273 B1
(45) Date of Patent: Apr. 1, 2003

(54) MULTIPLE SORBENT CARTRIDGES FOR SOLID PHASE EXTRACTION

(75) Inventor: Robert S. Plaisance, Clayton, NC (US)

(73) Assignee: Aventis CropScience, S.A., Lyons (FR)

( * ) Notice: Subject to any disclaimer, the term of this patent is extended or adjusted under 35 U.S.C. 154(b) by 71 days.

(21) Appl. No.: 09/711,210

(22) Filed: Nov. 9, 2000

Related U.S. Application Data

(60) Provisional application No. 60/165,376, filed on Nov. 12, 1999.

(51) Int. Cl.[7] ...................... G01N 30/14; G01N 30/400; G01N 30/50
(52) U.S. Cl. .................... 436/178; 210/198.2; 210/283; 210/290; 210/656; 210/662; 210/663; 422/70; 422/101; 436/98; 436/161; 73/23.41; 73/61.53; 95/88; 96/104
(58) Field of Search ................................. 436/178, 161, 436/98; 422/101, 70; 210/662, 663, 690, 691, 264, 283, 284, 290, 656, 198.2; 95/88; 96/104; 73/23.39, 23.41, 61.53

(56) References Cited

U.S. PATENT DOCUMENTS

| 4,803,215 A | 2/1989 | Jensen-Korte et al. ...... 514/407 |
|---|---|---|
| 4,806,144 A | 2/1989 | Schallner et al. ............... 71/92 |
| 4,806,540 A | 2/1989 | Sasse et al. ............... 514/236.5 |
| 4,808,209 A | 2/1989 | Gehring et al. ................. 71/92 |
| 4,808,623 A | 2/1989 | Ooms et al. ................. 514/404 |
| 4,810,283 A | 3/1989 | Gehring et al. ................. 71/92 |
| 4,810,720 A | 3/1989 | Jensen-Korte et al. ...... 514/407 |
| 4,812,165 A | 3/1989 | Schallner et al. ............... 71/92 |
| 4,820,725 A | 4/1989 | Jensen-Korte et al. ...... 514/407 |

(List continued on next page.)

FOREIGN PATENT DOCUMENTS

| DE | 2930516 | 2/1981 |
|---|---|---|
| EP | 0386926 | 9/1990 |

OTHER PUBLICATIONS

Chemical Abstract No. 1998:524339. Goldade et al, Book of Abstracts, 216th ACS National meeting, boston, Aug. 23–27 (1998), AGRO–071, Published by American Chemical Society, Washington, DC.*
Chemical Abstract No. 1992:542605. Beckert et al, Environ. Sci. Res. (1991), 42(Chem. Prot. Environ.), 113–26.*
Database WPI AN 1994–131983, abstract of JP 06 080594, published Mar. 22, 1994 (XP002160702).
Database WPI AN 1990–264481, abstract of JP 02 184695 published Jul. 19, 1990 (XP002160703).

*Primary Examiner*—Jan Ludlow
(74) *Attorney, Agent, or Firm*—Burns, Doane, Swecker & Mathis, L.L.P.

(57) ABSTRACT

Methods and apparatus are disclosed which are useful for detecting the presence of various pesticides, including aryl pyrazoles such as fipronil. Pesticide residues are extracted from a variety of samples, including soil and/or water samples using techniques well known to those of skill in the art. The samples are then concentrated, and transferred to an solid phase extraction cartridge. The SPE cartridge includes activated charcoal, silica gel, magnesium-silica gel and an amino-functional silica sorbent, or suitable equivalents thereof. After cleanup, the eluate containing the analyte of interest can be concentrated to a standard sample size and the amount of pesticide residues quantitated. In a preferred embodiment, the column chromatography materials are assembled in a solid phase extraction cartridge with frits between the chromatography materials. This facilitates the use of the cartridge in standard automated analytical equipment, for example, robotic equipment.

30 Claims, 1 Drawing Sheet

U.S. PATENT DOCUMENTS

| | | | |
|---|---|---|---|
| 4,863,937 A | 9/1989 | Gehring et al. | 514/333 |
| 4,868,198 A | 9/1989 | Ooms et al. | 514/406 |
| 4,877,439 A | 10/1989 | Gehring et al. | 71/86 |
| 4,908,377 A | 3/1990 | Jensen-Korte et al. | 514/404 |
| 4,909,832 A | 3/1990 | Gehring et al. | 71/92 |
| 4,931,461 A | 6/1990 | Jensen-Korte et al. | 514/404 |
| 5,167,691 A | 12/1992 | Maravetz | 71/92 |
| 5,496,956 A | 3/1996 | Woodard et al. | 548/377.1 |
| 5,536,700 A | 7/1996 | Woodward et al. | 504/128 |
| 5,675,017 A | 10/1997 | Hamper et al. | 548/377.1 |
| 5,696,144 A | 12/1997 | Royalty et al. | 514/404 |
| 5,750,704 A | 5/1998 | Shiokawa et al. | 546/275.1 |
| 5,869,688 A | 2/1999 | Hamper et al. | 548/377.1 |
| 5,880,290 A | 3/1999 | Hamper et al. | 548/377.1 |
| 5,883,263 A | 3/1999 | Hamper et al. | 548/377.1 |
| 5,900,489 A | 5/1999 | Hamper et al. | 548/377.1 |
| 5,910,596 A | 6/1999 | Mao | 548/377.1 |
| 5,922,751 A | 7/1999 | Cavalla et al. | 514/407 |

* cited by examiner

MULTIPLE SORBENT CARTRIDGES FOR SOLID PHASE EXTRACTION

This application claims benefit of U.S. Provisional Application No. 60/165,376, filed Nov. 12, 1999.

FIELD OF THE INVENTION

This application is generally in the area of solid phase extraction, more specifically, in the area of cartridges for use in solid phase extraction.

BACKGROUND OF THE INVENTION

Solid phase extraction uses analyte/sorbent interactions similar to those used in high performance liquid chromatography (HPLC). Solid phase extraction uses cartridges packed with a variety of sorbents, for example, surface-modified bonded silica sorbents, which selectively retain specific classes of chemical compounds from a group of compounds added to the cartridge. For example, strong cation exchangers can be used to retain cationic drugs, such as amphetamine, from urine samples. Some interactions between sorbent and analyte are relatively strong, for example, sorbents bonded to biotin strongly interact with streptavidin in an analyte sample.

Bonded silica sorbents are often used for chromatographic isolation, in part because a number of different functional groups can be readily bonded to the silica surface. Bonded silicas are also advantageous in that they are rigid supports and do not shrink or swell. Further, they have relatively large surface areas and are stable to a wide range of solvent conditions.

Solid phase extraction is commonly used to clean-up and concentrate compounds in analyte mixtures, and also to exchange solvent systems, for example, from aqueous to organic, at some point prior to a further analysis. Solid phase extraction can be used to achieve these goals.

Solid phase extraction consists of four basic steps, namely, conditioning, retention, rinsing and elution. Conditioning involves preparing a cartridge for reproducible interaction with a sample by solvating the sorbent bed. This is typically done by passing a volume of an appropriate solvent through the cartridge, and then passing through a volume of a solvent system similar to that used in the sample. For example, when conditioning a cartridge for use with aqueous samples, a volume of an alcohol such as methanol might be passed through the cartridge, followed by a volume of water. Retention involves applying the sample to the conditioned cartridge and allowing the compound of interest to be retained on the sorbent surface due to one or more specific chemical interactions. The interactions might be linkage of biotin to streptavidin, or Van der Waals interactions between the hydrocarbon chain of a compound of interest and a hydrocarbon chain on a C18 bonded phase. Components of the sample that bind with less affinity typically pass through the cartridge, resulting in purification of the sample. Rinsing involves passing solvents through the cartridge to rinse away additional compounds other than the compound of interest while leaving the compound of interest adhered to the sorbent bed. Water is commonly used as a rinse solvent for non-polar extractions performed on a C18 sorbent. Elution involves passing an appropriate solvent through the cartridge while it disrupts the interaction between the compound of interest and the sorbent, which allows the compound of interest to be selectively eluted from the cartridge. For non-polar extractions, organic solvents such as alcohols are generally strong enough solvents to disrupt the interaction between most non-polar analytes and a C18 bonded phase.

Automated equipment is often used to perform analytical analyses of a large number of analytes. Solid phase extraction cartridges have been designed which are capable of being used in automated equipment, such as robotic equipment. New sorbents and cartridge systems are constantly being generated for use in detecting the presence of various compounds, for example, environmental contaminants.

Analytical methods have been developed for determining the presence of aryl pyrazole insecticides such as fipronil in agricultural soil and filter paper plaques. However, the previously described methods are limited in that they are not automated, and therefore are limited in their usefulness for evaluating large numbers of soil samples. Moreover, there is a need in the art for analytical methods for determining the amount of pyrazoles in a variety of samples in the agricultural, pharmaceutical and other areas of science.

Thus, there is a continuing need for further analytical methods and detection systems which can be used in automated chemical analyses to detect the presence of potentially hazardous compounds in various environmental samples. The present invention provides such methods and detection systems.

SUMMARY OF THE INVENTION

Methods and apparatus are disclosed which are useful for detecting the presence of pesticides, such as pyrazoles including fipronil, in soil, water, blood, tissue, urine and other types of agricultural, medical or pharmaceutical samples. The methods and apparatus of the invention can be used in a wide variety of applications to purify and allow for the quantitation of the amount of pesticide, especially pyrazole, particularly aryl pyrazole, and its metabolites in a given sample.

The present invention provides an apparatus for solid phase chromatography comprising a column having a first opening for receiving a sample and a second opening for discharging an eluate, which column comprises a first separation zone containing amino-functional silica, a second separation zone containing activated carbon, a third separation zone containing magnesium-silica gel or silica gel and a fourth separation zone containing magnesium-silica gel or silica gel, whichever was not used in the third separation zone.

The activated carbon generally is pre-treated with hydrochloric acid prior to use in the apparatus of the invention. The amino-functional silica also generally is treated with organic solvent prior to placement in the apparatus of the invention. In one aspect of the invention, a fifth separation zone is provided containing a drying agent.

In another aspect of the invention, a method for removing aryl pyrazoles from a sample is provided which comprises extracting the aryl pyrazole residues from a sample in a solvent, concentrating the extract to form a concentrated extract, and subjecting the concentrated extract to solid phase chromatography on a column comprising a first separation zone containing amino-functional silica; a second separation zone containing activated carbon, a third separation zone containing magnesium-silica gel or silica gel and a fourth separation zone containing magnesium-silica gel or silica gel, whichever was not used in the third separation zone. The eluate eluting from the column after the chromatography will contain the aryl pyrazole residues and metabolites.

In another aspect of the invention, a method for determining the amount of pesticide residue in a sample is provided, comprising extracting the pesticide residues from a sample in a solvent; concentrating the extract to form a concentrated extract; transferring the concentrated extract to a column comprising a first separation zone containing amino-functional silica, a second separation zone containing activated carbon, a third separation zone containing magnesium-silica gel or silica gel and a fourth separation zone containing magnesium-silica gel or silica gel, whichever was not used in the third separation zone; subjecting the concentrated extract to solid phase extraction by passing at least one organic solvent through the column to obtain an eluate solution; removing the eluate solution from the column; and analyzing the eluate solution to determine the amount of pesticide residue.

In one aspect, the methods and apparatus of the invention may be utilized to isolate a pyrazole and its metabolites from a soil, water or other sample. Where the pyrazole is in a soil sample, the residues of the pyrazole first may be extracted using techniques well known to those of skill in the art. The extracts then are concentrated, and the samples are cleaned up or purified using solid phase extraction, using multiple sorbent cartridges to remove various components other than the compounds of interest (the aryl pyrazoles and their metabolites). The sorbent cartridges include amino-functional silica, activated carbon, magnesium-silica gel and silica gel, or suitable equivalents thereof.

In a preferred embodiment, the column chromatography materials are assembled in a solid phase extraction cartridge. Preferably, the cartridge is a twenty cubic centimeter cartridge. The components for the solid phase extraction can be packed in the cartridge with or without dividing elements between the various components. In one aspect of the invention, the cartridge has frits on top, on the bottom and between the chromatography materials. This facilitates shipping of the cartridges and the use of the cartridges in standard automated analytical equipment, for example, robotic equipment.

Using the methods and apparatus described herein, large numbers of samples can be analyzed in an automated fashion.

DETAILED DESCRIPTION OF THE INVENTION

Figure 1:
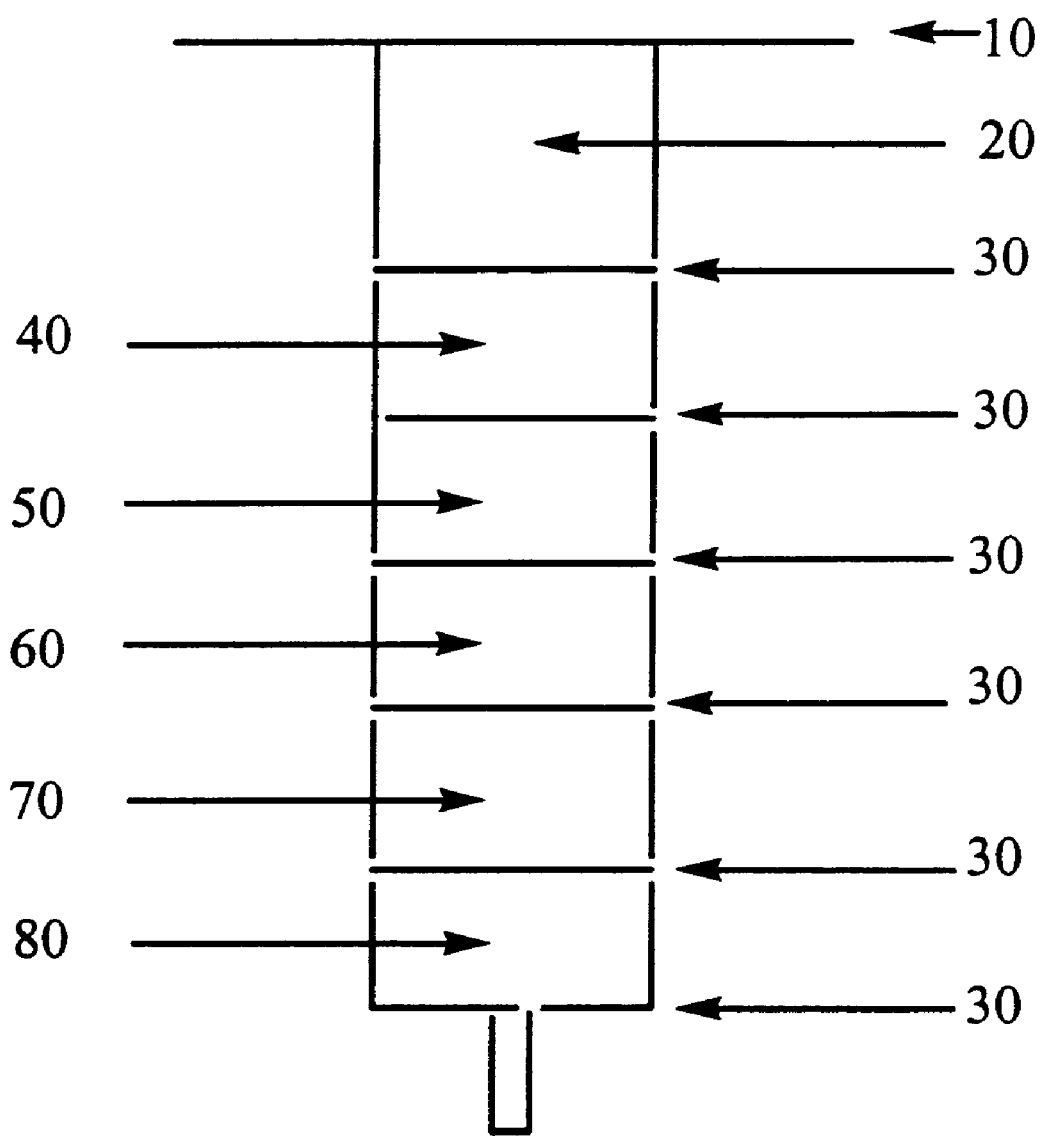
FIG. 1 is a side view of a 20 cc solid phase extraction cartridge as described herein.

The method and apparatus of the present invention enables the isolation of pesticides, such as aryl pyrazoles and/or their metabolites, from a variety of samples. The method and apparatus taught herein may be used by the agricultural community to quantitate the amount of pesticides in soil and water samples. The method and apparatus alternatively may be used by the medical and veterinary communities to isolate aryl pyrazoles from blood, tissue and urine. Isolation and quantification of these compounds has been difficult heretofore. The method and apparatus of the invention provides a simple procedure for isolating the pyrazoles which can be used in an automated system. Among the advantages of this method is that it permits the use of relatively smaller samples than can be analyzed using other analytical methods. For example, a 20 g soil sample can be analyzed using this method, rather than the 50 g sample required by other methods.

I. Soil Samples

The soil samples are those obtained from a site believed to contain pesticide residues. In a preferred embodiment, the soil samples are those which are believed to contain aryl pyrazole pesticide residues. As used herein, insecticide and pesticide are occasionally used interchangeably. Both are intended to be included. A suitable soil sample size is between 10 and 100 grams, preferably between 20 and 50 grams.

The detectable level of pesticide residues is about 0.002 ppm in agricultural soil, using gas chromatographic analysis with a mass selective detector. In filter paper plaques, the level is about 0.050 ppm.

When the aryl pyrazole to be isolated from a sample is a pesticide from a soil or water sample, pesticide residues first are extracted from the soil and/or water samples using techniques well known to those of skill in the art. One set of conditions for extracting aryl pyrazoles and their metabolites from soil samples involves extraction with 70:30 v/v acetonitrile:acetone. The samples can be concentrated in an automated manner, preferably using a Zymark Turbo-Vap with Turbo-Vap tubes. An automated robotic system, for example, a Zymark XP robot, can be used for sample concentration and solid phase extraction. Mass selective detectors are preferably used for analysis.

II. Pesticides which can be Evaluated

A. Aryl Pyrazoles

Aryl pyrazoles are known as pesticides and insecticides. Examples of aryl pyrazole pesticides and insecticides, and their metabolites, which can be detected in soil and water samples using the methods described herein include those described, for example, in U.S. Pat. Nos. 5,922,751, 5,910, 596, 5,900,489, 5,883,263, 5,880,290, 5,869,688, 5,750,704, 5,696,144, 5,675,017, 5,536,700, 5,496,956, 5,167,691, 4,931,461, 4,909,832, 4,908,377, 4,877,439, 4,868,198, 4,863,937, 4,820,725, 4,812,165, 4,810,720, 4,810,283, 4,808,623, 4,808,209, 4,806,540, 4,806,144, and 4,803,215.

A preferred insecticide is fipronil, 1H-pyrazole-3-carbonitrile, 5-amino-1-[2,6-dichloro-4-(trifluoromethyl) phenyl]-4-[(trifluoromethyl)sulfinyl]-. The presence of three known metabolites of this compound can also be assayed. These metabolites are available as analytical standards from Aventis CropScience. They are listed below by chemical name:

1H-pyrazole-3-carbonitrile, 5-amino-1-[2,6-dichloro-4-(trifluoromethyl)phenyl]-4-[(trifluoromethyl)thio]-;
1H-pyrazole-3-carbonitrile, 5-amino-1-[2,6-dichloro-4-(trifluoromethyl)phenyl]-4-[(trifluoromethyl)sulfonyl]-;
1H-pyrazole-3-carbonitrile, 5-amino-1-[2,6-dichloro-4-(trifluoromethyl)phenyl]-4-trifluoromethyl-.

B. Other Pesticides

Other pesticides which can be evaluated using the methods described herein include 1,2,4-triazinones, 1,3,5-triazines, 2-4-arylenephenoxy propionic acids, 2,6-dinitroanilines, 2-dimethylaminopropane-1,3-dithiol, 2-dimethylaminopropane-1,3-dithiol analogues, Acari, alkanamides, alkylenebis (dithiocarbamates), amides, amidines, aminoglycoside antibiotics, anilides, anilinopyrimidines, antibiotics, aromatic hydrocarbons, aromatic hydrocarbon derivatives, arylalanines, aryloxyalkanoic acids, aryloxyphenoxypropionic acids, auxin, avermectin, azoles, azole analogues, azomethine, bacterium, benzilate, benzimidazoles, benzimidazole precursors, benzofuranyl alkanesulfonates, benzoic acid derivatives, especially chlorinated derivatives, benzonitriles, benzoxazines, benzoylureas, bipyridyliums, bis-carbamates, carbamates, carboxamides, chloracetanilides, chloroamides, chlorophenols, Coleoptera, coumarin anticoagulants, coumarin anticoagulant analogues, cyclodiene organochlorines, cyclohexanedione oximes, cytokinins, diacylhydrazines, dicarboximides, imethylaminopropane-1,3-dithiol, dimethyldithiocarbamate, dinitroaniline, dinitrophenol, dinitrophenol derivatives, diphenyl ethers, Diptera, dithiocarbamates, DMI fungicides, entomopathogenic fungus, ethylene generators, fatty acids, fungi, granulosis viruses, guanidine, halogenated alkanoic acids, Hemiptera, hydroxybenzonitrile, hydroxybenzonitrile percursors, Hymenoptera, imidazolinones, indandione anticoagulants, inorganic compounds, for example, inorganic flourides, juvenile hormone mimics, methyl isothiocyanate precursors, morphactin, morpholine, morpholine analogues (piperidine derivatives), N-trihalomethylthio ompounds, natural pyrethrins, nematodes, Neuroptera, non-ester pyrethroids, nuclear polyhedrosis viruses, organoarsenic compounds, organochlorines, organophosphate esters, organophosphorus compounds, in particular, organophosphorus herbicides, organotin compounds, oxime carbamates, oxyacetamide, phenoxyquinoline, phenyl carbamates, phenylamides (in particular, the acylalanine and acylamino butyrolactone types), phenylamides (in particular, the acylamino coazolidinone type), phenylpyrazoles, phenylpyrroles, phenylureas, pheromones, phosphinico amino acids, phosphoramidates, phthalimides, phthalimide analogues, pyrazoles (acaricides), pyrazole (acaricide) analogues, pyrazoles (herbicides), pyrethroids, pyridazinone (including CBI and PSII), pyridine, pyridinecarboxylic acid, pyrimidine, pyrimidinyl carbinol, pyrimidinyloxybenzoic acids, pyrimidinyloxybenzoic acid analogues, quaternary ammonium salts, quinolinecarboxylic acids, strobilurin analogues, sulfamoylureas, sulfonylureas, synthetic auxins, tetrazines, thiocarbamates, triazines, triazinones, triazoles, triazolopyrimidine sulfonanilides, triketones, uracil, ureas, especially halogenated ureas, viruses, and wasps.

III. SPE Cartridge

The solid phase extraction is done using a cartridge specifically designed for use with pesticides, particularly aryl-pyrazole compounds. The cartridge described herein includes various components, including activated carbon, magnesium-silica, silica gel, and amino-functional silica. Other components may be used in the cartridge such as sodium sulfate or another suitable drying agent. It has been discovered that the use of these sorbents in a particular order in a solid phase extraction process enables the effective removal of aryl pyrazoles and their metabolites from a variety of sample materials. As used herein, sorbent means capable of taking up and holding by either absorption or adsorption.

The first separation zone or layer of sorbent material in the cartridge, from top to bottom, with the opening for passing the sample into the cartridge at the top of the cartridge column, contains an amino-functional silica. More particularly, the amino-functional silica may be silica with an aminopropyl bonded functional group. Silicas of this kind are known in the art and are commercially available, for example, from Alltech Associates, Inc., as the product "Amino". Amino has a particle size of about 35 to about 75 microns.

Generally, the amino-functional silica is purified or pretreated prior to use in the solid phase extraction of the invention by the following method: shaking the silica for about 5 minutes with organic solvent, for example, 1:1 v/v acetone/hexane, then filtering under vacuum until air dried, and storing in a sealed container. Generally, the organic solvent will be a solvent mixture which will contain at least one polar solvent and at least one nonpolar solvent. Solvent combinations such as various ratios of acetone, hexane, cyclohexane, acetonitrile, ethyl actetate, dichloromethane and pentane may be used. Preferably, the solvent mixture will include at least one ketone with 3 to 6 carbons optionally substituted by halogen and at least one $C_5$ to $C_{10}$ hydrocarbon solvent, provided the solvents are miscible with each other. Generally, the ketone will have a boiling point of less than about 70° C. at atmospheric pressure and the $C_5$ to $C_{10}$ hydrocarbon solvent will have a boiling point of less than about 85° C. at atmospheric pressure, preferably less than about 70° C. The solvents preferably will be used in a ratio of about 1:1 v/v of polar to non-polar solvent. In the most preferred embodiment, the solvent mixture is 1:1 v/v acetone and hexane. The purpose of the rinse solvent it to ensure the removal of water and surface impurities on the activated carbon.

Adsorption chromatography media for the removal of fats, lipids, triglycerides, proteins, carbohydrates, humic acids, glycol, etc., can also be used. The amount of amino-functional silica in the column or cartridge preferably will be about 1 g.

The second separation zone or layer in the solid phase extraction column or cartridge contains activated carbon. The activated carbon (charcoal) can be any type commercially available or known to those of skill in the art, such as Darco® or EnviCarb®. The activated carbon is preferably Darco®, 20–40 mesh, in granular form. It is commercially available from Aldrich Chemicals. It generally will be pretreated prior to use in the solid phase extraction of aryl pyrazoles by the following method: shaking the carbon with an about 3N aqueous acid solution such as HCl, at a ratio of about 50 grams carbon to about 100 mL HCl, for about 25 minutes, filtering the carbon under vacuum, rinsing with water until the pH adjusts to about 45, drying the carbon, for example, in a vacuum oven, and rinsing the carbon with an organic solvent or solvent mixture, for example, 1:1 v/v acetone/hexane, before drying at about 130° C. for about 48 hours. The drying preferably is conducted in an oven. The pH preferably is verified prior to proceeding to the next step in the pretreatment process. The amount of water needed to rinse about 50 g of carbon to obtain a pH of about 4 to about 5 is about 500 mL. Generally, the solvent mixture will contain at least one polar solvent and at least one nonpolar solvent. Solvent combinations such as various ratios of acetone, hexane, cyclohexane, acetonitrile, ethyl actetate, dichloromethane and pentane may be used. Preferably, the solvent mixture will include at least one ketone with 3 to 6 carbons optionally substituted by halogen and at least one $C_5$ to $C_{10}$ hydrocarbon solvent, provided the solvents are miscible with each other. Generally, the ketone will have a boiling point of less than about 70° C. at atmospheric pressure and the $C_5$ to $C_{10}$ hydrocarbon solvent will have a boiling point of less than about 85° C. at atmospheric pressure, preferably less than about 70° C. The solvents preferably will be used in a ratio of about 1:1 v/v of polar to non-polar solvent. In the most preferred embodiment, the solvent mixture is 1:1 v/v acetone and hexane.

The amount of activated carbon in the cartridge preferably will be about 2 g.

The third and fourth separation zones, or chromatographic layers, will contain magnesium-silica gel or silica gel. These components can be interchanged such that the magnesium-silica gel may be the third layer and the silica gel may be the fourth layer or the silica gel may be the third layer and the magnesium-silica gel may be the fourth layer. The magnesium-silica gel can be any of this type of silica known in the art. Preferably, the magnesium-silica gel is Florisil®, which is an extremely white, hard powdered magnesium-silica gel. This type of magnesium-silica gel may also be referred to a magnesium silicate and typically contains silicone dioxide, magnesium oxide and sodium oxide. The Florisil® used is preferably 60/100 mesh, PR Grade, from US Silica Company. It may be activated by heating overnight at about 130° C. Preferably, the amount of magnesium-silica gel and the amount of silica gel will be about 2 g of each component.

The silica gel of the third or fourth separation zone or layer is preferably silica gel 60, about 63 to about 200 microns, about 70 to about 230 mesh, from ICN Adsorbents. It may be dried by heating overnight at around 130° C.

An optional fifth layer may be present in the solid phase extraction cartridge of the invention. For example, a drying agent may be present in a fifth layer. This layer may be present at the top of the column of sorbents. Sodium sulfate (anhydrous) is preferably used as a drying agent, although other drying agents can also be used, for example, magnesium sulfate, molecular sieves, and diatomaceous earth, such as Hydromatrix™ from Varian Corporation. The amount of drying agent will depend on the particular drying agent selected. Preferably, the amount will be about 2 to about 7 g. of drying agent in the cartridge. However, if sodium sulfate is used, the amount will be closer to about 7 g. but if molecular sieves or diatomaceous earth is used, the amount will be lower, about 2 g.

The sorbents of the invention may be provided in a solid phase extraction cartridge or column by any means known to those of skill in the art. The sorbent materials must be placed in the cartridge in the order described above in order for the extraction of the aryl pyrazoles and their metabolites to be effective. However, the sorbent materials may be placed in the cartridge with or without a physical means for separating the layers from each other. Rather the cartridge or column may be prepared with only a frit or other seal means at the bottom, below all the sorbents, and at the top of the column of sorbents. If physical barriers are desired between the layers, they may be any of the known types of materials utilized in solid phase extraction methods. For example, filter paper or frits may be used. Frits have been found preferable for purposes of maintaining the positions of the sorbents during shipping. The frit used may be any of those known for use in solid phase chromatography or in other scientific applications.

III. Analytical Method

The following examples describe the extraction of pesticides from soil samples, but these procedures can be adapted to apply to a variety of samples, including water, blood, urine and tissue, among others.

A. Extraction of Pesticides from Soil Samples

Soil samples are weighed, and a standard sample size (preferably about 20 g) is extracted using the same solvent system, preferably in the same volume, for each sample. A solvent system useful for extracting 1-arylpyrazoles is 70:30 v/v acetonitrile/acetone. The extraction is preferably performed using an extractor, for example, a Dionex Accelerated Solvent Extractor (ASE). ASE is a method for the extraction of test compounds from solid matrices such as soils. ASE is a fully automated system, requiring smaller quantities of solvent than traditional methods.

The sample can be extracted using mechanical shaking as follows. 100 ml of a 70/30 v/v acetonitrile/acetone mixture can be added to a 20 gram soil sample. The sample can then be centrifuged for a suitable amount of time at a suitable number of revolutions per minute. An example of suitable conditions is 3500 RPM for five minutes. The solvent can be decanted, and an additional 50 mL solvent added. The soil sample can be shaken for a suitable amount of time on a mechanical shaker (for example, about 15 minutes), and centrifuged as above. The solvent can then be decanted.

When using a Dionex Accelerated Solvent Extractor, additional components can be added to the soil sample to facilitate extraction. For example, for 20 grams of soil, 2.75 grams Hydromatrix™ (diatomaceous earth) and 4 grams of granular sodium sulfate can be added. The following are suitable parameters for using with a Dionex Accelerated Solvent Extractor. The temperature can be any temperature between room temperature and just below the boiling point of the solvent used for the extraction, but is preferably around 50° C. The pressure is about 1500 psi. Other extraction systems are known and may be used for extraction of the sample from which the pyrazole and its metabolites are to be removed.

Filter plaques can be prepared by inserting filter paper samples into a suitable receptacle, for example, a labeled jar. For fortification/recovery, the samples can be fortified with acetonitrile. For 0.009 M filter paper, an appropriate amount of acetonitrile is about 500 mL. For 0.3 M filter paper, an appropriate amount of acetonitrile is about 1000 mL. The fortified samples can be shaken for a suitable amount of time (for example, about 60 minutes on a mechanical shaker), and an aliquot of the acetonitrile solution prepared for GC/MSD analysis or other suitable means for quantifying the amount of pesticide residues. The solvents used for the extraction can also be concentrated as above.

B. Concentration of Solvent

After decantation, the solvent can be concentrated to a reasonable volume (typically about 5 mL) for transfer to an SPE cartridge for clean-up. The concentration can be performed using any of a variety of known methods, for example, centrifugation, vacuum distillation, and passage of an inert gas over the surface of the solvent. A Turbo Vap system from Zymark is particularly preferred for concentrating the solvent.

C. Re-dissolving of the Concentrated Analyte

After the extraction solvent is concentrated, the residue (the analyte) is either placed directly on the SPE column described herein, or re-dissolved in a small amount of an appropriate solvent for use in the solid phase extraction. Examples of suitable solvents include acetone, methanol, acetonitrile and ethyl acetate.

D. Solid Phase Extraction

The concentrated residues are added to an SPE cartridge to minimize the amount of proteinaceous materials and other components present in soil. The solid phase extraction is performed by passing the analyte in solution in an appropriate solvent through a solid phase extraction cartridge. One embodiment of the cartridge of the invention is shown in FIG. 1. As shown in FIG. 1, Part 10 is an SPE cartridge/column. Part 20 is a void volume. Parts 30 are a series of frits. Part 40 is a layer of a drying agent. Part 50 is a layer of activated carbon. Part 60 is a layer of amino-functional silica. Part 70 is a layer of silica gel or magnesium-silica. Part 80 is a layer of magnesium-silica or silica gel, whichever was not used in the above layer.

In one embodiment, the cartridge includes a space or opening for receiving a sample or an analyte solution, which is followed by a frit, then sodium sulfate, then another frit, then activated carbon such as Darco® carbon, then another frit, then Amino, then another frit, then silica gel or Florisil®, then another frit, then Florisil® or silica gel (the opposite of what was in the last stage), then a final frit. The total volume of the cartridge is preferably about 20 cc, although it can be larger for applications other than use in automated analyses.

Prior to adding the analyte solution, the cartridge is conditioned by passing a suitable volume of solvent through the cartridge. For example, about 25 mL methanol, followed by 25 mL of acetone, followed by 30 mL of acetonitrile can be added to the column. Other useful solvents and volumes for use in conditioning the column include 25 mL of hexane, 25 mL of cyclohexane, 25 mL of ethyl acetate, or 25 mL of toluene.

Next, the concentrated solvent is transferred directly onto the SPE cartridge, and the tube containing the concentrated solvent is preferably rinsed with an appropriate solvent and the rinsate added to the SPE cartridge. Then, as the analyte passes through the cartridge, an additional two to four volumes of acetonitrile or other appropriate solvent can be passed through the SPE column. The slower the flow rate through the column, the more clean-up of the sample. Rates of 1–2 mL per minute are particularly desirable.

Various impurities are retained on the amino-functional silica, the magnesium-silica and the silica gel, and various impurities are removed by the carbon plug. The aryl pyrazoles and their metabolites or other pesticides are eluted by passing an appropriate solvent through the cartridge, as discussed above. The eluate contains any pyrazole or metabolites contained in the initial sample and may be used for further analysis.

E. Analysis

The eluate is then concentrated as described above, and the final volume is kept constant between samples to ensure consistency. The eluate is then analyzed for pesticide content, preferably by GC/MS, although other methods are known and may be used. Suitable conditions for performing the GC/MS are well known to those of skill in the art.

F. Automation

The above method, or various stages thereof, can be automated. For example, one can prepare a plurality of SPE cartridges, have robotic arms transfer the solvents to and from the various stages in the method, add solvents to various tubes using automated pipetting systems, and transfer tubes to and from various test tube racks, for example, containing analyte samples from the SPE cartridges, from the evaporator, and the like. Robotic systems for automating the method are well known to those of skill in the art, and include those manufactured by Zymark, Inc.

The following examples are given to illustrate the invention and should not be construed to limit the scope of the invention.

EXAMPLE

Fipronil and its metabolites were analyzed using the methods and apparatus of the present invention. Soil was analyzed for possible residues of fipronil and its non-polar metabolites. Residues were extracted from agricultural soil with 70:30 (v/v) acetonitrile:acetone. After concentration of the extract, column chromatography using activated carbon, amino-functional silica, magnesium-silica gel and silica gel was utilized for clean-up. Filter paper plaques were extracted with acetonitrile. The acetonitrile was analyzed at a specified final volume. Quantification of fipronil and its metabolites was accomplished by gas chromatography using a mass selective detector.

The following reagents were used:

1. Activated carbon (charcoal), Darco®, 20–40 mesh, granular, Aldrich, Cat. No. 24,226-8. The activated carbon was purified by shaking the carbon with ~3 N HCl (50 g to 100 mL) for ~25 minutes, then filtering it under vacuum, and then generously rinsing with distilled water until the pH of the water coming through the carbon was at least pH 4–5. The carbon was then dried with vacuum before it was rinsed with 50:50 acetone:hexane (v/v). The carbon then was oven dried at ~130° C. for ~48 hours.
2. Amino, Alltech, 35–75 μm, Part No. 211516. The amino was purified by shaking the amino for about five minutes with 50:50 acetone:hexane (v/v) and filtering it under vacuum until it was air dried. The amino was then stored in a sealed glass jar.
3. Florisil® 60/100, PR Grade, US Silica Company. The Florisil® was activated by heating it overnight at about 130° C.
4. Silica Gel 60, 63–200 micron, 70–230 mesh, ICN Adsorbents, Cat. No. 04663. The silica gel was dried by heating it overnight at about 130° C.
5. Sodium sulfate, anhydrous, granular analytical reagent, Mallinckrodt Cat. No. 8024.
6. Hydromatrix® (Chem-Elut), Varian, Part Number CE2A048.

The column chromatography materials were assembled in a twenty cubic centimeter solid phase extraction cartridge with frits by Supelco.

The following solvents were used:

1. Acetonitrile UV, B & J High Purity Solvents, Burdick & Jackson, Cat. No. AH015-4.
2. Acetone, B & J Chrompure HPLC Solvent, Burdick & Jackson, Cat. No. AH010-4.
3. Methanol, B & J Chrompure HPLC Solvent, Burdick & Jackson, Cat. No. AH230-4.
4. A 70:30 acetonitrile:acetone solution was prepared by mixing 700 mL of acetonitrile with 300 mL of acetone.

The following equipment was used:

1. Aluminum Crimp-Top Seal, 11 mm TFE/RUB Septum, Sun Brokers, Inc.
2. Analytical Balance, weigh accurately to ±1 mg, and an analytical balance to weigh accurately to ±0.1 mg.
3. Autosampler vials, 1 mL, clear.
4. Dionex Accelerated Solvent Extractor (ASE).
5. Dionex Cell Body and Cap assembly.
6. Dionex Cell Body Filters, grade D28.
7. Dionex ASE sample vials, 60 mL.
8. Dionex ASE, sample collection vial cap.
9. Dionex retaining ring.
10. Dionex O-ring.
11. ICHEM, Teflon silica septa.
12. VWR 50 mL voumetric flask.
13. Disposable Pasteur Pipets.
14. Class "A" volumetric flasks, various sizes, with ground glass joint stoppers.
15. Mechanical shaker.
16. Brinkmann Dispensette, 5–50 mL.
17. Nalgene® 250 mL screw-capped bottles, Nalge Co.
18. Turbo Vap® Concentration Workstation, Zymark, with concentrator tubes, 200 mL with 1 mL endpoint.
19. Volumetric pipets.
20. Separatory funnels, 125 or 250 mL.
21. Hewlett Packard 6890 Series GC equipped with Hewlett Packard 5973 Series Mass Selective Detector equipped with autosampler and computer.

22. Glass liner, glass wool, 6.5 mm×78.5 mm.
23. Capillary column, 30 m×0.25 i.d., 0.25 μm film thickness.
24. Filter paper, Whatman number 2 or number 3, 0.09 m and 0.3 m.
25. ½ GL PP Mason Jar.
26. Graduated cylinders, class "A", 1000 or 2000 milliliters.
27. SPE adaptor.
28. Stopcocks.
29. Boiling flasks, 24/40 ground glass joint, 100, 250, or 500 mL.
30. Tongs or forceps, spatula or spoon.
31. Chromatography column with stopcock and reservoir.

Standard solutions of fipronil and its metabolites were prepared according to known methods for use as fortification standards and calibration standards. Twenty grams of soil were weighed into a labeled 250 mL Nalgene® screw cap bottle and 100 mL of 70:30 (v/v) acetonitrile:acetone solution was added. The solution was centrifuged at 3500 RPM for five minutes.

The extraction solvent was decanted into a labeled Zymark Turbo Vap® tube. 50 mL of 70:30 (v/v) acetonitrile:acetone was added and the mixture was shaken for 15 minutes on a mechanical shaker and then centrifuged at 3500 RPM for five minutes. The extraction solvent was then decanted into an appropriate Zymark Turbo Vap® tube. The extract was then concentrated to 5 mL using the Turbo Vap® at a temperature of 45° C. and a pressure of 1.1 bar.

A solid phase extraction cartridge was prepared as follows: The cartridge was injection molded and the components for the solid phase extraction were each weighed and placed in the cartridge in the following order bottom to top: silica gel, Florisil®, Darco®, Amino and sodium sulfate, with a frit on the bottom, in between layers and on the top. The top frit has a plastic retaining ring which operated to hold the materials in place with the necessary amount of compression.

A Varian stopcock was attached to the SPE cartridge and the SPE cartridge was attached to the URG SPE adaptor. The reservoir/cartridge assembly was supported with a clamp. A boiling flask was then attached to the SPE adaptor. A 125 mL separatory was suspended above the SPE assembly. The Varian stopcock was opened and a slight vacuum was initiated to give a flow rate of 1–3 mL/min. The column was conditioned with 25 mL of methanol, which was repeated with 25 mL of acetone and 30 mL of acetonitrile. When the acetonitrile reached the top of the amino, the stopcock was closed. The boiling flask was removed and the washes discarded as needed.

A clean, labeled Zymark Turbo Vap® tube was placed under the SPE cartridge and the vacuum was turned off. The concentrated extract was transferred directly onto the column using a disposable Pasteur pipet. The Zymark Turbo Vap® tube was then rinsed with 10 mL of acetonitrile and transferred to the column using 3 mL increments to ensure thorough rinsing of the tube. The stopcock was opened until the level of the extract reached the top of the amino and then it was closed. The Zymark Turbo Vap® tube containing the extract was rinsed with 70 mL of acetonitrile UV and transferred to the cartridge/reservoir. The stopcock was opened again until the level of the extract reached the top of the amino and then it was closed. The column flow rate was 1–2 milliliters per minute.

The Zymark Turbo Vap® tube was then prepared for Turbo Vap® evaporation. The acetonitrile was evaporated to 1–2 mL and transferred to a labeled class "A" 5.0 mL volumetric flask. Additional acetonitrile was used to rinse the Zymark Turbo Vap® tube and then this was transferred to the volumetric flask. The volume was adjusted to 5.0 mL, the flask was capped and the contents were mixed by shaking and inverting the flask several times. An aliquot of the eluate from the flask was prepared for GC/MSD analysis to quantify the amount of fipronil and its metabolites in the eluate. The GC/MS analysis was conducted according to known methods.

While the invention has been described in detail and with reference to specific embodiments thereof, it will be apparent to one skilled in the art that various changes and modifications can be made without departing from the spirit and scope thereof.

What is claimed is:

1. An apparatus for solid phase chromatography comprising a column having a first opening for receiving a sample and a second opening for discharging an eluate, which column comprises:
   a. a first separation zone containing an amino-functional silica;
   b. a second separation zone containing activated carbon;
   c. a third separation zone containing magnesium-silica gel or silica gel; and
   d. a fourth separation zone containing magnesium-silica gel or silica gel, whichever was not used in the third separation zone.

2. The apparatus of claim 1, wherein the column has a volume of approximately 20 cc.

3. The apparatus of claim 1, further comprising a fifth separation zone before the first separation zone which contains a drying agent.

4. The apparatus of claim 3, wherein the drying agent is selected from the group consisting of sodium sulfate, magnesium sulfate, molecular sieves, and diatomaceous earth.

5. The apparatus of claim 1, wherein the activated carbon is pretreated by shaking the activated carbon with an about 3N HCl solution, at a ratio of about 50 grams activated carbon to about 100 mL HCl solution, for about 25 minutes, filtering the activated carbon under vacuum, rinsing with about 500 mL of water until the pH adjusts to about 4–5, drying the activated carbon, rinsing the activated carbon with organic solvent, and then drying at about 130° C. for about 48 hours.

6. The apparatus of claim 1, wherein the activated carbon is 20–40 mesh, in granular form.

7. The apparatus of claim 1, wherein the amino-functional silica is pretreated with organic solvent.

8. The apparatus of claim 7, wherein the amino-functional silica has a particle size of about 35 to about 75 microns.

9. The apparatus of claim 1, wherein the magnesium-silica is 60/100, PR Grade.

10. The apparatus of claim 1, wherein the silica gel has a particle size of between 70–230 mesh.

11. A method for removing aryl pyrazoles from a sample comprising:
   a. extracting the aryl pyrazole residues from a sample in a solvent;
   b. concentrating the extract to form a concentrated extract; and
   c. subjecting the concentrated extract to solid phase chromatography on a column comprising a first separation zone containing amino-functional silica, a second separation zone containing activated carbon, a third separation zone containing magnesium-silica gel or silica gel and a fourth separation zone containing magnesium-silica gel or silica gel, whichever was not used in the third separation zone.

12. The method of claim 11, wherein the column further comprises a fifth separation zone before the first separation zone which contains a drying agent.

13. The method of claim 12, wherein the drying agent is selected from the group consisting of sodium sulfate, magnesium sulfate, molecular sieves, and diatomaceous earth.

14. The method of claim 11, wherein the activated carbon is pretreated by shaking the activated carbon with an about 3N HCl solution, at a ratio of about 50 grams activated carbon to about 100 mL HCl solution, for about 25 minutes, filtering the activated carbon under vacuum, rinsing with about 500 mL of water until the pH adjusts to about 4–5, drying the activated carbon, rinsing the activated carbon with organic solvent, and then drying at about 130° C. for about 48 hours.

15. The method of claim 11, wherein the activated carbon is 20–40 mesh, in granular form.

16. The method of claim 11, wherein the amino-functional silica is pretreated with organic solvent.

17. The method of claim 16, wherein the amino-functional silica has a particle size of about 35 to about 75 microns.

18. The method of claim 11, wherein the magnesium-silica is 60/100, PR Grade.

19. The method of claim 11, wherein the silica gel has a particle size of between 70–230 mesh.

20. The method of claim 11, wherein the column has a volume of approximately 20 cc.

21. A method for determining the amount of pesticide residue in a sample comprising:

a. extracting the pesticide residues from a sample in a solvent;

b. concentrating the extract to form a concentrated extract;

c. transferring the concentrated extract to a column comprising a first separation zone containing amino-functional silica, a second separation zone containing activated carbon, a third separation zone containing magnesium-silica gel or silica gel and a fourth separation zone containing magnesium-silica gel or silica gel, whichever was not used in the third separation zone;

d. subjecting the concentrated extract to solid phase extraction by passing at least one organic solvent through the column to obtain an eluate solution;

e. removing the eluate solution from the column; and f. analyzing the eluate solution to determine the amount of pesticide residue.

22. The method of claim 21, wherein the method is automated.

23. The method of claim 21, wherein eluate is analyzed using gas chromatography and mass spectrometry.

24. The method of claim 21, wherein the activated carbon is pretreated by shaking the activated carbon with an about 3N HCl solution, at a ratio of about 50 grams activated carbon to about 100 mL HCl solution, for about 25 minutes, filtering the activated carbon under vacuum, rinsing with about 500 mL of water until the pH adjusts to about 4–5, drying the activated carbon, rinsing the activated carbon with organic solvent, and then drying at about 130° C. for about 48 hours.

25. The method of claim 21, wherein the activated carbon is 20–40 mesh, in granular form.

26. The method of claim 21, wherein the amino-functional silica is pretreated with organic solvent.

27. The method of claim 26, wherein the amino-functional silica has a particle size of about 35 to about 75 microns.

28. A column for use in solid phase chromatography with a top and a bottom and having a first opening for receiving a sample and a second opening for discharging an eluate which comprises, in order from the top to the bottom of the column, a first layer containing amino-functional silica, a second layer containing activated carbon, a third layer containing silica gel or magnesium-silica gel and a fourth layer containing silica gel or magnesium-silica gel, whichever was not used in the third layer.

29. The column of claim 28 wherein a physical barrier is located between the layers and on the top and bottom of the layers.

30. The column of claim 29 wherein the physical barrier is a frit.

\* \* \* \* \*